United States Patent [19]

Krbechek et al.

[11] Patent Number: 5,081,155

[45] Date of Patent: Jan. 14, 1992

[54] HYDROXY AROMATIC KETONES

[75] Inventors: Leroy Krbechek, Santa Rosa; Wilson Lin, Vallejo, both of Calif.

[73] Assignee: Henkel Corporation, Ambler, Pa.

[21] Appl. No.: 539,290

[22] Filed: Jun. 15, 1990

Related U.S. Application Data

[63] Continuation of Ser. No. 337,590, Apr. 13, 1989, abandoned.

[51] Int. Cl.$^5$ .............................................. A61K 31/12
[52] U.S. Cl. .................................... 514/689; 568/337
[58] Field of Search ............... 568/337; 514/689, 688; 71/122

[56] References Cited

U.S. PATENT DOCUMENTS

| | | | |
|---|---|---|---|
| 2,258,556 | 10/1900 | Schirm | 568/337 |
| 3,335,164 | 8/1967 | Scherer et al. | 568/337 |
| 3,705,177 | 12/1972 | Chodnekar et al. | 568/337 |
| 4,219,570 | 8/1980 | Inayuka et al. | 514/688 |
| 4,390,537 | 6/1983 | Cragoe | 514/689 |

FOREIGN PATENT DOCUMENTS

| | | | |
|---|---|---|---|
| 3629056 | 3/1987 | Fed. Rep. of Germany . | |
| 51-10021 | 9/1976 | Japan | 514/689 |
| 394241 | 11/1965 | Switzerland | 568/337 |
| 1458695 | 12/1976 | United Kingdom | 568/337 |
| 2169807 | 7/1986 | United Kingdom . | |

OTHER PUBLICATIONS

Chem. Abstracts Index, p. 2108cs, vol. 10th, col. 1.
John S. Preston & Zofia B. Luklinska, Solvent Extraction of Copper (II) with Orthohydroxyoximes-I, J. Inorg. Nucl. Chem., pp. 431–439, 1980.
Soviet Inventions Illustrated, Section Chemical, week E16, Abstract No. 32241 E/16, 2 Jun. 1982, Derwent Publ. Ltd. GB; & SU-A-777889 (Med Parasit Trop Me) 30.11.1981.
M. Fieser: "Reagents for Organic Synthesis", vol. 10, pp. 135, 136, Wiley-Interscience, 1982, New York, U.S., p. 135, lines 5–8.
Chemical Abstracts: vol. 102, No. 13, 1 Apr. 1985, p. 669, JP 59-175,448 Formula Index vol. 102, vol. 102F1, p. 1331F, col. 1, lines 34–35; col. 2, lines 117, 118; vol. 102F2, p. 1607F, col. 3, lines 55, 56.
Chemical Abstracts: vol. 111, No. 19, 6 Nov. 1989, p. 437, Abstract No. 171146s, A. P. Rauter et al: "Flavonodis from Artemisia Campestris Subsp. Maritima", & Phytochemistry, 1989, vol. 28, No. 8, pp. 2173–2175.
Chemical Abstracts Service Registry Handbook, 1965–1971, registry numbers 35-66-5 through 4599-9-9-9, Columbus, Ohio, U.S., p. 824R, col. 3, lines 17, 18.
Chemical Abstracts: vol. 58, No. 6, 18 Mar. 1963, p. 5550b, Columbus, Ohio, U.S.; P. Demerseman et al.: "Thymol. XVI. Physicochemical Preparation and Study of some Methyl-and Ethylisopropylphenols", & Bull. Soc. Chem. France, 1962, pp. 1700–1705.

*Primary Examiner*—James H. Reamer
*Attorney, Agent, or Firm*—Ernest G. Szoke; Wayne C. Jaeschke; Patrick J. Span

[57] ABSTRACT

Novel hydroxy-aryl ketones are disclosed having a branched hydrocarbon chain on the aromatic nucleus ortho to the hydroxy group. The compounds were found to possess anti-microbial properties and are also useful as intermediates to the preparation of the corresponding oximes. The compounds are ideally defined by the formula:

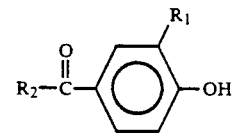

where $R_1$ is a saturated or unsaturated, branched chain hydrocarbyl group and $R_2$ is a saturated or unsaturated, straight or branched chain, hydrocarbyl group.

18 Claims, No Drawings

HYDROXY AROMATIC KETONES

This application is a continuation of application Ser. No. 07/337,590 filed on Apr. 13, 1989 now abandoned.

BACKGROUND OF THE INVENTION

1. Field of the Invention

This invention relates to novel hydroxy aromatic ketones having a branched hydrocarbon chain on the aromatic nucleus ortho to the hydroxy group which unexpectedly were found to possess anti-microbial properties and accordingly are useful as a general disinfectant.

2. Statement of Related Art

The use of chemicals as general disinfectants is well known and widely applied. Toxic chemicals are used to ensure sanitary conditions in hospitals, homes and work areas. These anti-microbial compositions are used both to reduce the number of viable microorganisms in the area, and to prevent the proliferation of microorganisms. A variety of disinfectants and antiseptic materials are known and available for use in the regard as anti-microbial agents. Such materials vary widely in character and range from relatively mild compositions suitable for topical applications on the human skin to very harsh materials suitable only for surface area applications to such areas as walls, floors, etc.

The hydroxy aromatic ketones of this invention are also useful as intermediates in the preparation of the corresponding oximes. Thus the compounds are useful for the preparation of hydroxy oximes of the type described in British Patent 1,322,532. As described therein the process proceeds according to the following reaction scheme:

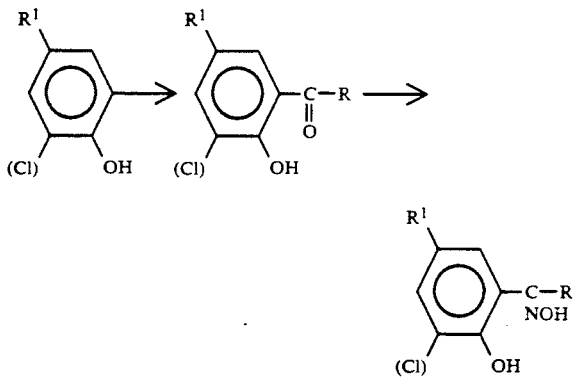

The patent thus describes the preparation of oximes from ketones such as alkyl 2-hydroxy-5-alkylphenyl ketones, such as methyl 2-hydroxy-5-nonylphenyl ketones. In order to function as extractants for metal values as disclosed therein, the oxime group

and hydroxyl group must be in an ortho relationship to each other. If in a para relationship the oxime will not complex with the metal values so as to extract them from their aqueous solution. As shown above, the $R^1$ alkyl group is in a para relationship to the hydroxyl group. As a practical matter in commercial practice the starting phenol material may contain some material in which the $R^1$ group is ortho to the hydroxyl group and will carry through the intermediate ketone to the final oxime product. Such product having no utility as an extractant has been removed and discarded along with other impurity by-products of reaction.

Similarly British Patent 1,551,619 describes the preparation of oximes from 2-hydroxy-5 alkyl phenyl alkyl ketones.

British Patent 1,458,695 describes the production of hydroxyketones and specifically the 2-hydroxy-5-alkyl-phenyl alkyl ketones such as methyl 2-hydroxy-5-tert-nonylphenyl ketone, from phenyl esters of the general formula:

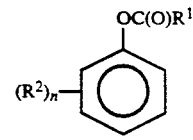

where $R^1$ is a substituted or unsubstituted hydrocarbyl group and $R^2$ is an alkyl substituent having a tertiary or quaternary carbon atom and n is 1, 2 or 3. While a general reference is made to $R^2$ occupying a position ortho, meta or para with respect to the $-OC(O)R^1$ group in the ester, the patent states the group in the para position produces very good results and all of the examples describe production of 2-hydroxy-5-alkyl ketone products, in which the alkyl group is para to the hydroxyl group, the hydroxyl group being ortho to the ketone group

BRIEF DESCRIPTION

Other than in the operating examples, or where otherwise indicated, all numbers expressing quantities of ingredients or reaction conditions used herein are to be understood as modified in all instances by the term "about".

It has now been found that hydroxy aromatic ketone compounds where the relative position of the hydroxy group and the hydrocarbyl group attached to the phenyl ring are in the 4-hydroxy-3 hydrocarbyl position, and the hydrocarbyl group is branched, the compounds possess anti-microbial properties, whereas compounds in the 2-hydroxy-5 hydrocarbyl position do not exhibit anti-microbial properties. Further, if the hydrocarbyl group is a straight chain rather than branched chain group, regardless whether in the 3- or 5- position, the compound does not exhibit anti-microbial properties. Thus, the compounds of the present invention require the relative position of 4-hydroxy-3-hydrocarbyl and that the hydrocarbyl group in the 3- position be branched. Thus, the hydroxyl group is in the para position relative to the ketone group and the hydrocarbyl group is ortho to the hydroxyl group. The compounds of the present invention are ideally defined by the formula

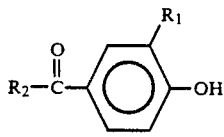

where $R_1$ is a saturated or unsaturated branched chain hydrocarbyl group and $R_2$ is a saturated or unsaturated, straight or branched chain hydrocarbyl. The maximum carbon chain length of the R group, $R_1$ and $R_2$ is not critical and is limited as a practical matter to compounds which are available having the appropriate desired group from which to prepare the compounds. As a practical matter $R_1$ will be a branched aliphatic hydrocarbon group containing from 5-22 carbon atoms and preferably 8 to 12 carbon atoms; while $R_2$ will be an aliphatic hydrocarbon group containing 1 to 22, and preferably 1-6 carbon atoms.

In use in anti-microbial disinfectant compositions the compounds are formulated with other ingredients found in disinfectant compositions such as solvents, perfumes, surfactants, and the like.

DETAILED DESCRIPTION AND PREFERRED EMBODIMENTS

As noted above, the compounds of the present inventions are defined by the formula

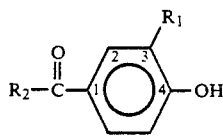

where $R_1$ and $R_2$ are as earlier defined. As can be seen from the formula the $R_1$ group is ortho in relation to the hydroxyl group and the hydroxyl group is para in relation to the ketone,

group.

$R_1$ is a saturated or unsaturated branched chain hydrocarbyl group, generally aliphatic hydrocarbon, having from 5-22 carbon atoms and preferably 8-12 carbon atoms. The preferred compounds are those in which $R_1$ is derived from a branched oligomer of propene, particularly the trimer, or isobutene, particularly the dimer or trimer. The propene trimer will contain 9 carbon atoms usually a mixture of differing branched chain isomers, hereinafter referred to as "isononene." It may also be described as a mixture of branched chain alkyl isomers containing 9 carbon atoms. The propene tetramer or pentamer may also be employed. The oligomers from isobutene will be a dimer containing 8 carbon atoms and the trimer containing 12 carbon atoms. The $R_1$ group may be viewed as having an aliphatic hydrocarbon main chain having branching substituents in which the branches contain from about 1-6 carbon atoms.

The $R_2$ group, as indicated earlier, may be a straight or branched chain, saturated or unsaturated hydrocarbyl group, generally an aliphatic hydrocarbon group containing from 1 to 22 carbon atoms and preferably 1-6 carbon atoms. Illustrative $R_2$ groups are methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonyldecyl and eicosane. Preferably $R_2$ is a linear or straight chain aliphatic hydrocarbon group having 1-10, most preferably 1-5 carbon atoms. However, $R_2$ may be branched and unsaturated. Representative but not exhaustive examples are those noted for $R_1$, above as branched, saturated or unsaturated groups. Of the various $R_2$ groups, methyl is the most preferred.

A preferred method of preparation of the instant compounds of this invention is to react a 4-alkyl phenol with an olelfin. The 4-alkyl phenolic compounds are commercial available. The most preferred is 4-ethylphenol which will result in $R_2$ being a methyl group. The alkyl phenol used should thus be selected with regard to the moiety desired for $R_2$, i.e.

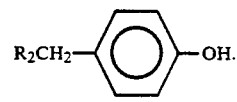

Similarly, the olefin is appropriately selected to give the structure desired for the $R_1$ moiety, i.e. to provide

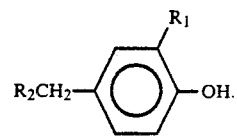

The alkyl moiety of the 4-alkyl phenol should have a secondary carbon atom at the alpha position. This alkyl group is then oxidized after the addition of the olefin $R_1$ moiety to give the (C=O) and the $R_2$ group.

Appropriate conditions for the reaction adding the olefin to the phenolic ring to give $R_1$ are temperatures in the range of from 60° to 100° C. and pressures in the range of 1-10 atmospheres. The products is then subjected to oxidation with a suitable oxidizing agent under an inert atmosphere, such as nitrogen. Suitable oxidizing agents are selected from the group consisting of dicyano, dichlorobenqoquinone, tetrachlorobenzoquinone, and lead tetra acetate. The above described reagents are preferably used at a 1:2 equivalents ratio of phenol to oxidizing agent. The oxidation proceeds at room temperature and accordingly elevated temperatures are not necessary. Temperatures up to 150° may be employed. If desired, any hydrocarbon solvent can be used. However, alcohols such as the alkanols containing 1-5 carbon atoms, are preferred, particularly methanol.

When conducting a Friedel-Crafts reaction with an alkylated phenol and an acyl halide, problems arise with dealkylation of the alkyl group resulting in only small amounts of the desired product. However, under appropriate conditions the alkylated phenol may be esterified, and, with a Fries rearrangement of the ester under appropriate conditions, the desired product may be obtained starting with the ortho-alkyl phenol which contains some para-alkyl, the process can be conducted resulting in a mixture of para and ortho product from which the ortho product is then separated and recovered. While not the most efficient means of preparation, if the process of the British Patent 1458645 is employed with a para-alkyl phenol which contains some ortho-alkyl, the process can be conducted resulting in a mixture of para and ortho product from which the ortho product is then separated and recovered.

In the rearrangement process, the alkylated phenol is converted to the ester, preferably the acetate ester using acetic anhydride. The resulting ester is then washed to remove the byproduct acetic acid. The ester, in an organic (preferably hydrocarbon) solvent solution such as toluene, is heated to reflux and any remaining water removed azeotropically. Aluminum chloride is added and the HCl gas evolved is removed rapidly to minimize any dealkylation. The mixture, crude ketone, is quenched and washed with water and stripped of solvent. The washed crude ketone is then fractionated to provide the desired acetophenone product. As earlier indicated, the acetophenone is an intermediate to the corresponding oxime which is prepared by conventional oximation using hydroxylamine sulfate and caustic or sodium acetate.

When the instant compounds are used as antimicrobial agents, they can be applied at 100% concentration or can be mixed with a carrier or solvent in a sufficient amount to ensure an effective anti-microbial capacity in the final mixture. Extremely dilute concentrations can be used. Acceptably, therefore, the instant anti-microbial compounds can be applied or used in a carrier or solvent at concentrations from 1% up to 100% by weight. An acceptable minimum concentration for the instant compounds in an anti-microbial composition, therefore, is 1% by weight.

Preferably, a solvent is used which will ease use and application of the composition. Representative but nonexhaustive examples of appropriate solvents are alcohols (alkanols having 1-6 carbon atoms); ketones; aromatic hydrocarbon solvents, such as benzene, xylene, toluene; and straight chain aliphatic hydrocarbon solvents such as hexane, heptane, decane, and dodecane. Alcohols such as isopropyl alcohol are commonly employed. The concentration range of the instant antibacterial compounds should preferably be in the range of from about 5 to about 50% by weight (wt.) and most preferably in the range of from about 15 to about 30% by wt.

Additives can appropriately be used in addition to a carrier or solvent or instead of a carrier or solvent. Such additives can be used to give the particular anti-bacterial blend distinct and desired characteristics. Surfactants, for example, can be used in an effective amount which will give the compositing a detergent capability. Suitably, the surfactant is nonionic. Preferably, surfactants can be selected from the group consisting of alkylpoyoxyethylene glycol, ethoxylated aliphatic alcohol, ethoxylated aliphatic alcohol, ethoxylated aliphatic alcohol, ethoxylated fatty alcohol ethers, polyoxyethylated nonylphenol, ethoxylated oleyl alcohol, ethoxylated tridecyl alcohol, polyoxyethylated sorbitan monolaureate, polyoxyethylated sorbitan monopalmitate, polyoxyethylene sorbitan monostearate, polyoxyethylene sorbitan tristearate, polyoxyethylene sorbitan monooleate, polyoxyethylene sorbitan mono and tri oleate, alkylaryl polyether, sorbitan monolaureate, sorbitan monopalmate, sorbitan monostearate, sorbitan trimonostearate, sorbitan monooleate, and sorbitan trioleate.

Other appropriate additives which could be used if desired are compounds which give fragrance or act as air fresheners. Suitable fragrances can be selected from the group consisting of: amyl salicylate, benzyl acetate, benzyl butyrate, benzyl propionate, phenyl ethyl isobutyrate, phenyl ethyl propionate, citralnitrile, isoamyl acetate, isobutyl benzoate, isononyl acetate, linalyl acetate, and n-butyl heptanoate.

Additives can be blended with the instant antibacterial compounds in any convenient manner or order. For effective anti-microbial activity, the additives should be used so that a one phase liquid is obtained.

The instant invention will be more fully understood from the examples which follow. These examples are intended to clarify the instant invention and not to limit it. All parts and percentages are by weight unless otherwise specified.

EXAMPLE 1

3-isononyl-4-hydroxyacetophenone was prepared by the following method: A 37 g. quantity of 4-ethylphenol (30 millimoles) was heated with 2 ml concentrated sulfuric acid in a 500 ml flask to about 60° C. A 44 g. (35 millimoles) quantity of isononene was added and the mixture was heated to between 60° and 70° C. for two hours. Water, 250 milliliters (ml), and 250 ml of ether were added to cool the solution. The organic layer was washed with sodium bicarbonate solution and dried over magnesium sulfate. The solvent was removed under vacuum distillation and the remaining oily substance was then distilled also under vacuum. The distillate, 3-isononyl-4-ethylphenol, was collected over the temperature of 115°-120° C. under 0.4 mm of mercury. 1 gram (4 millimoles) of this 3-isononyl-4-ethylphenol was mixed with 50 ml of methanol and treated with 1.8 grams (8.0 millimoles) of dicyano-dichlorobenzoquinone under nitrogen. The reaction mixture was stirred at room temperature for eight hours under nitrogen. The methanol was removed under vacuum to give solids which were extracted with benzene. The filtrate was evaporated to give an oil which was chromatographed on silica gel with 10% ether in methyl chloride to give 250 mg of 3-isononyl-4-hydroxyacetophenone.

EXAMPLE 2

A lawn of microorganisms was grown on nutrient agar plates using the following microorganisms: Pseudomonas, aeruginosa ATCC 27853 to *Escherichia coli* ATCC 25922, *Staphylococcus aureus* ATCC 25923 and *Bacillus Subtilis* (lab isolate).

After 24 hours of growth on the plate, a small quantity (about 10 milligrams) of 3-isononyl-4-hydroxyacetophenone was spotted in one area of the plate. Chlorine and gluteraldehyde, two known anti-microbial agents, were also spotted on the plate as controls. The plates were then incubated at 37° C. for 48 hours.

Very definite zones of inhibitions were indicated around all three agents thus demonstrating the antimicrobial properties of all three agents.

EXAMPLE 3

In comparison, other isomers similar to the compounds to the instant invention were tried as antimicrobials. The results of these compounds are reported under this example in samples A, B and C.

Samples A, B and C were all tested using the same procedure as is described in Example 2 and these samples were all tested on microorganisms of the same species and source as is described in Example 2.

SAMPLE A 3-n-nonyl-4-hydroxyacetophenone was also tested as an anti-microbial. There was no indication of any inhibition of the previously indicated microorganisms by the 3-n-nonyl-4-hydroxyacetophenone. The chlorine and the gluteraldehyde, however, showed normal inhibition of these microbes.

SAMPLE B 2-hydroxy-5-isononylacetophenone was tested as an anti-microbial agent in the same manner.

There was no indication that the 2-hydroxy-5-isononylacetophenone had any anti-microbial activity against the previously described microbes. The chlorine and gluteraldehyde, however, exhibited normal anti-microbial activity.

SAMPLE C 3-isononyl-4-hydroxyacetophenone oxime was prepared and tested as an anti-microbial agent.

The 3-isononyl-4-hydroxyacetophenone oxime failed to act as an anti-microbial agent, and showed no effect on the previously described microorganisms. The chlorine and gluteraldehyde, however, showed normal inhibition to these microorganisms.

We claim:

1. An hydroxy aryl ketone compound having the general formula:

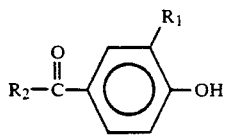

wherein $R_1$ is a branched chain aliphatic hydrocarbyl group containing from 8 to 12 carbon atoms and $R_2$ is a straight or branched chain aliphatic hydrocarbyl group containing from 1 to 22 carbon atoms.

2. A ketone as defined in claim 1 where $R_2$ contains from 1 to 6 carbon atoms.

3. A ketone as defined in claimed in claim 2 wherein $R_1$ contains 9 carbon atoms and $R_2$ is a methyl.

4. A ketone as defined in claimed in claim 2 wherein $R_1$ contains 12 carbon atoms and $R_2$ is methyl.

5. A ketone as defined in claimed in claim 1 wherein $R_1$ and $R_2$ are saturated.

6. A ketone as defined in claimed in claim 1 wherein $R_1$ and $R_2$ are unsaturated.

7. A ketone as defined in claimed in claim 1 wherein $R_1$ is unsaturated and $R_2$ is saturated.

8. A ketone as defined in claimed in claim 1 wherein $R_1$ is saturated and $R_2$ is unsaturated.

9. A ketone as defined in claim 1 wherein $R_2$ is a straight chain.

10. A ketone as defined in claim 1 wherein $R_2$ is a branched chain.

11. 3-isononyl-4-hydroxyacetophenone.

12. An anti-microbial composition comprising the ketone defined in claim 1.

13. An anti-microbial composition comprising a solvent solution containing a minimum of 1% by weight of the ketone defined in claim 1.

14. An anti-microbial composition as defined in claim 13 wherein said solution contains said ketone in an amount of about 5 to 50% by weight.

15. An anti-microbial composition as defined in claim 14 wherein said ketone is present in an amount of about 15 to 30% by weight.

16. An anti-microbial composition as defined in claim 13 wherein said solvent is selected from the group of alcohols, ketones, aromatical aliphatic hydrocarbon solvents.

17. An anti-microbial composition as defined in claim 13 wherein said solvent is an alkanol containing from 1 to 6 carbon atoms.

18. An anti-microbial composition as defined in claim 17 wherein said solvent is isopropanol.

* * * * *

UNITED STATES PATENT AND TRADEMARK OFFICE
CERTIFICATE OF CORRECTION

PATENT NO. : 5,081,155
DATED : January 14, 1992
INVENTOR(S) : Leroy Krbechek et al.

It is certified that error appears in the above-identified patent and that said Letters Patent is hereby corrected as shown below:

In claim 3, at column 8, line 3, "in claimed" should be deleted.

In claim 4, at column 8, line 5, "in claimed" should be deleted.

In claim 5, at column 8, line 7, "in claimed" should be deleted.

In claim 6, at column 8, line 9, "in claimed" should be deleted.

In claim 7, at column 8, line 11, "in claimed" should be deleted.

In claim 8, at column 8, line 13, "in claimed" should be deleted.

Signed and Sealed this

Twentieth Day of July, 1993

Attest:

MICHAEL K. KIRK

Attesting Officer    Acting Commissioner of Patents and Trademarks